United States Patent [19]
Rosenberg

[11] Patent Number: 4,857,060
[45] Date of Patent: Aug. 15, 1989

[54] PROTECTIVE DEVICE FOR HYPODERMIC NEEDLE

[76] Inventor: Michael E. Rosenberg, 121 Tekening Dr., Tenafly, N.J. 07670

[21] Appl. No.: 206,117

[22] Filed: Jun. 13, 1988

[51] Int. Cl.⁴ .............................................. A61M 5/32
[52] U.S. Cl. ..................................... 604/192; 604/263
[58] Field of Search ........................ 604/192, 187, 263

[56] References Cited
U.S. PATENT DOCUMENTS
4,573,975  3/1986  Frist et al. ............................ 604/192

*Primary Examiner*—John D. Yasko
*Attorney, Agent, or Firm*—W. Patrick Quast

[57] ABSTRACT

A protective device, for a hypodermic needle having a cylinder with a plunger coaxial along an axis, and an end wall with a projecting needle, is provided. The device has an annular, radially projecting web portion of fabric or plastic material, which has a radially inner edge and a radially outer edge. The device has a collar, which is joined to the radially inner edge. The collar is mounted on the cylinder end wall. The device also has a closing drawstring, which is threaded inside a turned-in edge portion of the radially outer edge of the web portion. The web portion has first, second third, and fourth rigid members, composed of a plastic material or the like. The first rigid member has a bent end portion. The rigid members form a box-like structure around the needle, when the web portion is in a closed condition. The rigid portions each have beveled side edges. The cylinder has an adhesive tape for holding taut the drawstring, when the web portion is in a closed condition. The cylinder end wall has a neck portion, on which the collar is mounted. The neck portion has a tapered portion supporting the needle. When the needle is withdrawn from the skin of a patient, the protective device prevents blood from the puncture from coming into contact with the operator of the hypodermic needle.

8 Claims, 2 Drawing Sheets

PROTECTIVE DEVICE FOR HYPODERMIC NEEDLE

The invention generally relates to a protective device for a hypodermic needle, and in particular the invention relates to a protective device for a hypodermic needle having a parachute-like portion around the needle.

BACKGROUND OF THE INVENTION

The prior art protective device for a hypodermic needle is described in U.S. Pat. No. 4,139,009 issued Feb. 13, 1979. Related patents include U.S. Pat. Nos. 2,876,770, issued Mar. 10, 1959; 2,925,083, issued Feb. 16, 1960; 2,937,643, issued May 24, 1960; 3,134,380 issued May 26, 1964; 3,406,687, issued Oct. 22, 1968; 4,160,450, issued July 10, 1979; and 4,642,099, issued Feb. 10, 1987.

The prior art protective device for a hypodermic needle, which has a syringe assembly that has a cylinder with a needle on the outside thereof and a piston on the inside thereof, is a bellows assembly, which covers the needle as the needle is moved into and out of the skin.

One problem with the prior art protective device for a hypodermic needle is that the protective device does not cover the puncture and the area of the skin disposed around the needle, so that an operator is not protected from any blood from the puncture or on such area of the skin.

SUMMARY OF THE INVENTION

According to the present invention, a needle protective device for a hypodermic needle is provided. The device comprises an annular, radially projecting, web member having an axis and having a radially inner edge and having a radially outer edge, a collar connected to the radially inner edge for connection to the hypodermic needle, and closing means connected to the radially outer edge for closing the web member after the hypodermic needle is withdrawn from the skin. By using the annular, radially projecting web member, the area of the skin disposed around the needle is covered, so that an operator is protected from any blood from the puncture or on the surrounding area of skin.

The foregoing and other objects, features and advantages will be apparent from the following description of the preferred embodiment of the invention as illustrated in the accompanying drawings.

DESCRIPTION OF THE PREFERRED EMBODIMENT

Figures 1, 2:
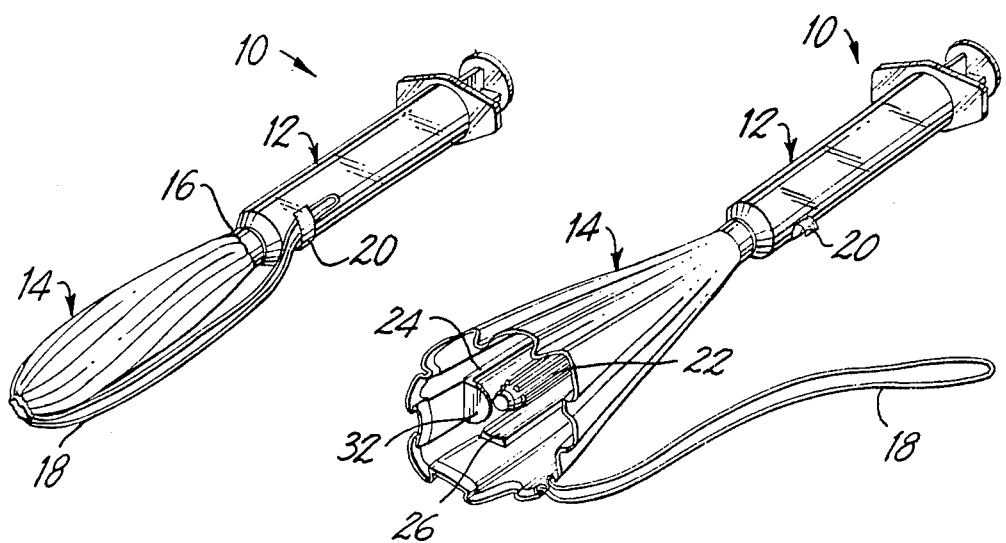
FIG. 1 is a perspective view of a protective device for a hypodermic needle according to the invention.
FIG. 2 is another perspective view corresponding to FIG. 1 with the device in a partly open condition.

As shown in FIGS. 1 and 2, an apparatus 10 according to the invention is provided. Apparatus 10 includes a syringe assembly or hypodermic needle assembly 12, which has an axis 8, and a cylinder 9, and a plunger or piston 11. Apparatus 10 also includes a parachute shaped, needle protective device 14. Device 14 has a peripheral web member 15, which is composed of a flexible material. Web member 15 has a radially inner edge portion 17 and has a radially outer edge portion 19. Device 10 also has a collar member 16, which has a hinge-like connection to the radially inner edge portion 17. Device 10 also has a closing member or a drawstring 18, which is connected to the radially outer edge portion 19. Syringe 12 has a holder or an adhesive tape 20, which holds drawstring 18.

Cylinder 9 has a needle 21, which has a conventional, removable needle cover 22.

Figure 3:
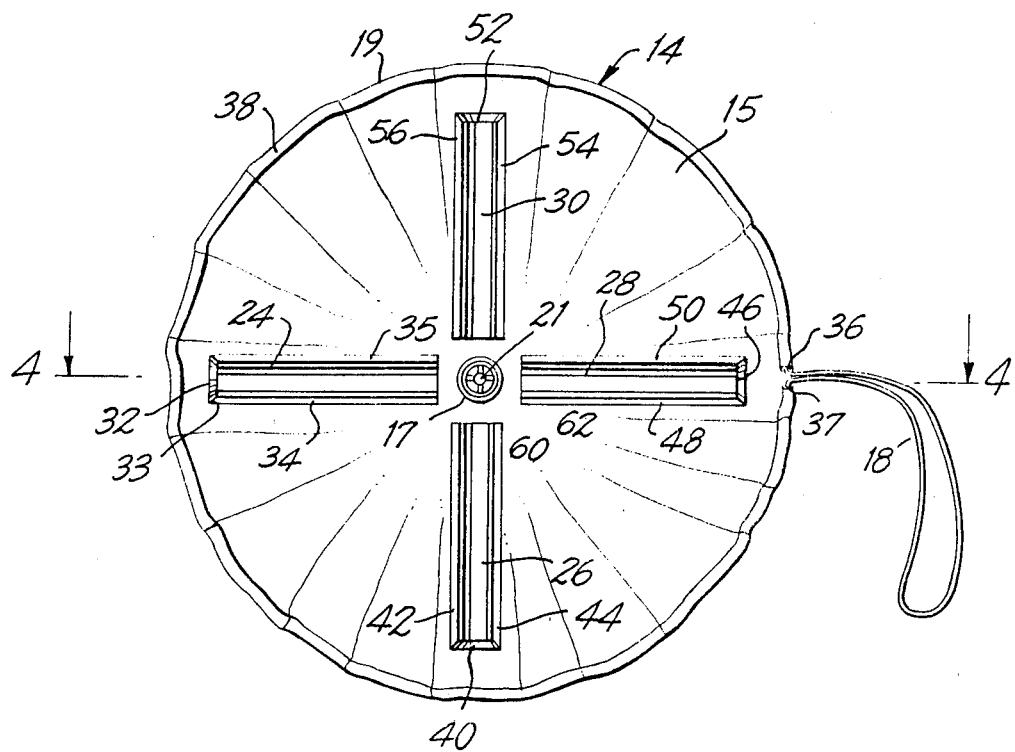
FIG. 3 is a bottom view of the protective device of FIG. 2 with the device in a fully open condition.

In FIG. 3, device 14 has respective first, second, third, and fourth rigid portions 24,26,28,30, each of which has an arcuate shape in section. Rigid portions 24, 26, 28, 30 form a box-like structure around needle 21 when device 14 is in a closed position. Rigid portion 24 has a bent portion or extension 32, which has a beveled or chamfered end edge 33 and which has two beveled side edges 34, 35.

Web 15 has two openings 36, 37 for drawstring 18 which are located at the opposite ends of a turned-in edge portion 38.

Rigid portion 26 also has one beveled end edge 40 and two beveled side edges 42, 44. Rigid portion 28 also has one beveled end edge 46 and two beveled side edges 48, 50. Rigid portion 30 also has one beveled end edge 52 and two beveled side edges 54, 56. Rigid portions 24, 26, 28, 30 are joined to web portion 15 by a connection means, such as an adhesive, or the like.

Figure 4:
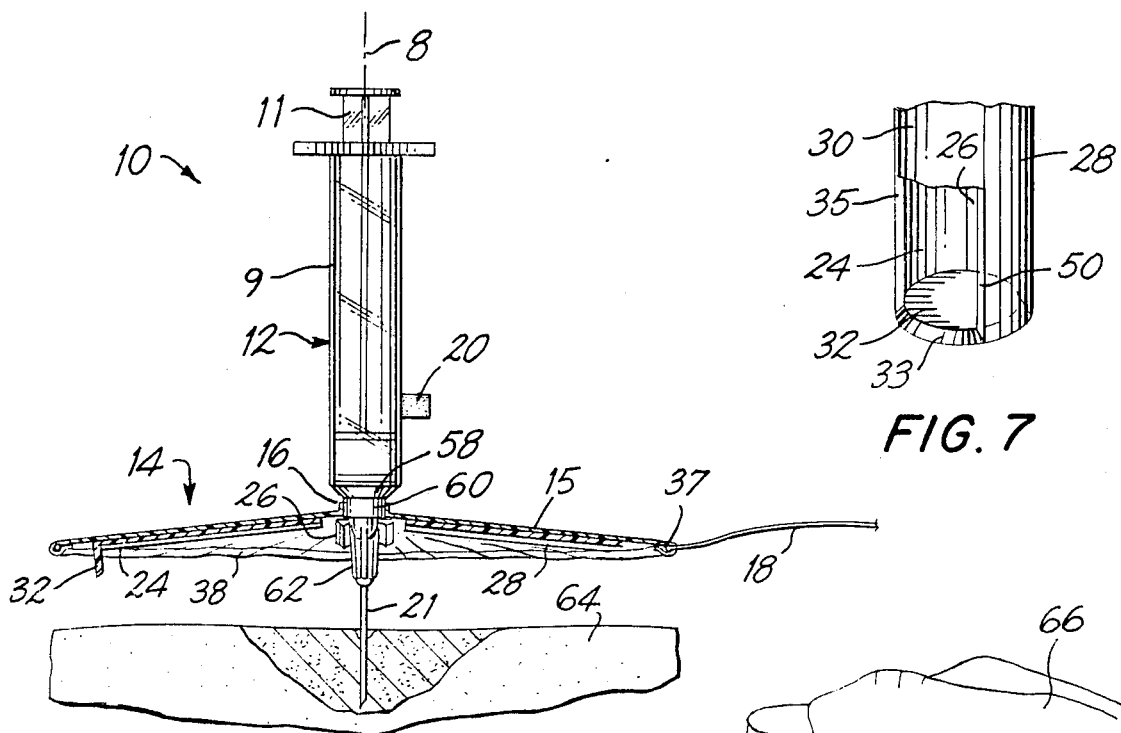
FIG. 4 is a section view as taken along the line 4—4 of FIG. 3.
Figure 7:
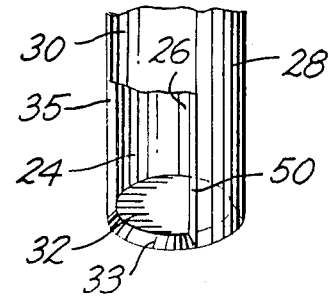
FIG. 7 is an enlarged perspective view of a portion of FIG. 6.

In FIGS. 3 and 4, cylinder 9 has an end wall 58, which has a neck portion 60, to which collar 16 is joined. Neck 60 has a tapered portion 62, that supports needle 21.

In FIG. 4, needle 21 is shown inserted into skin 64. Web portion 15 is shown as extended in a fully open condition. Thus, any blood portion, which is sprayed from or flows from an area of skin around needle 21 will be covered by web portion 15, thereby protecting the operator of the apparatus 10 from contact with the blood portion.

Figure 5:
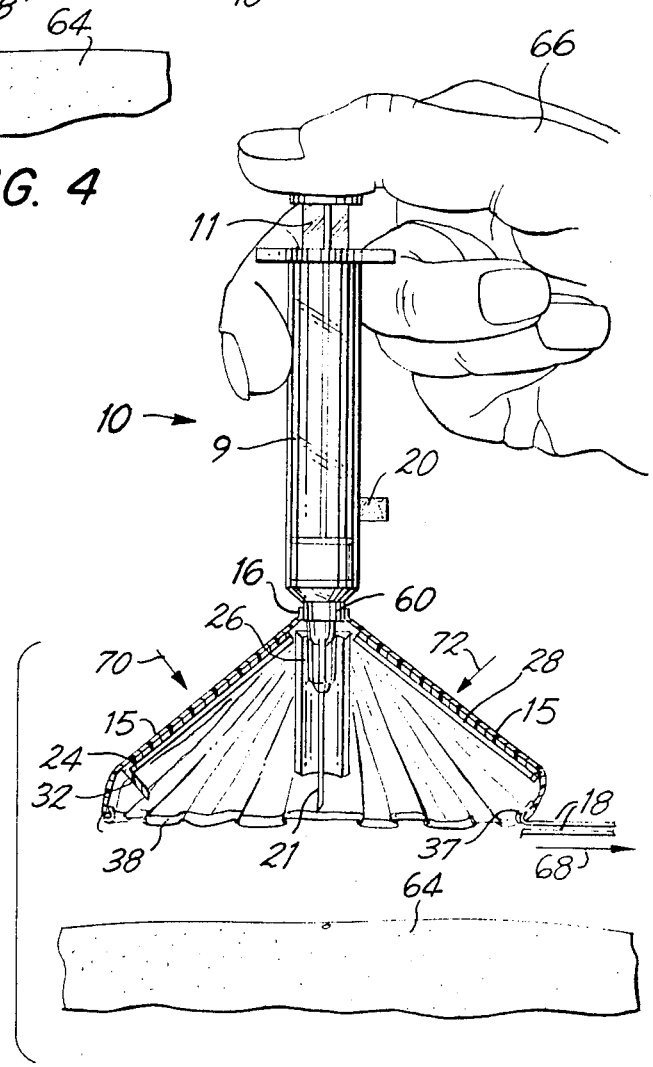
FIG. 5 is a section view corresponding to FIG. 4 with the device in a partly closed condition.

In FIG. 5, apparatus 10 is held by the right hand 66 of an operator. Hand 66 grasps cylinder 9 and piston 11 at their upper end portions. The thumb of hand 66 presses down on piston 11 to move piston downwardly relative to cylinder 9. Cylinder 9 and piston 11 form a chamber for containing a liquid or drug, which is forced through needle 21 into skin 64, when piston 11 is moved downwardly relative to cylinder 9. Cylinder 9, in this embodiment, is composed of a transparent material, such as a transparent plastic material. Piston 11 is composed of a similar material.

In FIG. 5, after needle 21 is withdrawn from skin 64, web portion 15 is gradually closed by applying a tension force 68 on both end portions of drawstring 18. In FIG. 5, the left side of web portion 15, moves in a closing direction 70, and the right side of web portion 15 moves in a closing direction 72, as force 68 is applied by the left hand (not shown) of the operator on the end portions of drawstring 18.

Figure 6:
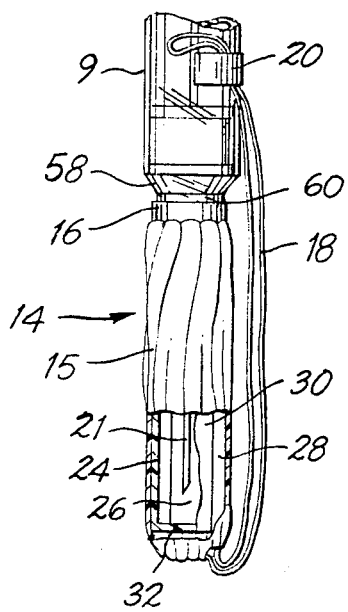
FIG. 6 is an elevation view of part of the device of FIG. 1.

In FIG. 6, tape 20 holds drawstring 18, when web portion 15 is in a closed condition, in order to keep web portion 15 fully closed.

The advantages of apparatus 10 are indicated hereafter.

First, protective device 14 covers the puncture and the area of skin 64 around needle 21, when needle 21 is inserted and withdrawn from skin 64, thereby preventing any blood, from the puncture or located on the area of skin surrounding needle 21, from coming into contact with an operator of apparatus 10.

Second, protective device 14 encloses needle 21 inside a box-like structure, made of arcuate rigid portions 24, 26, 28, 30, after protective device 14 is closed over needle 21, after needle 21 is withdrawn from skin 64.

Third, the device 14 is a safeguard against the transmission of a disease, such as the disease termed AIDS, caused by blood from a patient coming into contact with a medical person.

While the invention has been described in its preferred embodiment, it is to be understood that the words which have been used are words of description rather than limitation and that changes may be made within the purview of the appended claims without departing from the true scope and spirit of the invention in its broader aspects.

The embodiments of an invention in which an exclusive property or right is claimed are defined as follows:

1. A device for protecting a hypodermic needle having a cylinder and a plunger and an end wall with a needle coaxially disposed along an axis comprising:

an annular, radially projecting, web member coaxially disposed about the hypodermic needle, said web member having a radially inner edge portion and a radially outer edge portion;

a collar having a hinge-like connection to the radially inner edge portion, said collar connecting to the hypodermic needle; and, closing means connected to the radially outer edge portion for closing the web portion after the hypodermic needle is withdrawn from a skin puncture.

2. The device of claim 1, wherein said web portion has a plurality of radially oriented rigid portions.

3. The device of claim 2, wherein said rigid portions are elongate members connected to the web portion.

4. The device of claim 3, wherein said plurality of rigid portions are peripherally spaced and have a first rigid portion having a bent end portion for forming a box-like structure around the needle when the web portion is closed.

5. The device of claim 4, wherein the closing means includes a turned-in eqge portion on the radially outer edge and includes a drawstring disposed within the turned-in edge portion, the drawstring having end portions for closing the web portion upon the application of a tension force to the end portions of the drawstring.

6. The device of claim 5, wherein the hypodermic needle has a holder for holding taut the drawstring, when the web portion is in a closed condition.

7. The device of claim 6, wherein the rigid portions each have two beveled side edges.

8. The device of claim 7, wherein the cylinder end wall has a neck portion to which the collar is joined, and the neck portion has a tapered portion for supporting the needle.

* * * * *